US008052761B2

(12) United States Patent
Veatch

(10) Patent No.: US 8,052,761 B2
(45) Date of Patent: Nov. 8, 2011

(54) PROSTHETIC SPLIT HOOK TERMINAL DEVICE WITH ADJUSTABLE PINCH FORCE, FUNCTIONAL GRASPING CONTOURS AND ILLUMINATION

(75) Inventor: Bradley Delton Veatch, Westminster, CO (US)

(73) Assignee: Invisible Hand Enterprises, LLC, Westminster, CO (US)

( * ) Notice: Subject to any disclaimer, the term of this patent is extended or adjusted under 35 U.S.C. 154(b) by 89 days.

(21) Appl. No.: 12/467,098

(22) Filed: May 15, 2009

(65) Prior Publication Data

US 2009/0287316 A1    Nov. 19, 2009

Related U.S. Application Data

(60) Provisional application No. 61/053,537, filed on May 15, 2008.

(51) Int. Cl.
*A61F 2/54* (2006.01)
*A61F 2/68* (2006.01)
(52) U.S. Cl. .......................................................... 623/64
(58) Field of Classification Search ................ 623/57–65
See application file for complete search history.

(56) References Cited

U.S. PATENT DOCUMENTS

| 1,042,413 | A | | 10/1912 | Dorrance |
| 1,183,413 | A | * | 5/1916 | Visel ................................ 623/65 |
| 1,378,578 | A | | 5/1921 | Bauman |
| 1,390,802 | A | * | 9/1921 | McKay ........................... 623/65 |
| 1,465,933 | A | | 8/1923 | Dedic |
| 1,466,487 | A | | 8/1923 | Shaffer |
| 1,608,689 | A | | 11/1926 | Apel |
| 1,819,317 | A | * | 8/1931 | Baehr .............................. 623/65 |
| 1,981,698 | A | | 11/1934 | Henning |
| 2,098,481 | A | | 11/1937 | Baird |
| 2,382,403 | A | | 8/1945 | Eberle |
| 2,409,884 | A | | 10/1946 | Mollenhour |
| 2,549,074 | A | | 4/1951 | Fishbein et al. |

(Continued)

FOREIGN PATENT DOCUMENTS

DE                901583           1/1954

(Continued)

OTHER PUBLICATIONS

Miguelez et al., "The Transradial Anatomically Contoured (TRAC) Interface: Design Principles and Methodology," Journal of Orthotists and Prosthetists, vol. 15(4), 2003, pp. 148-157.

(Continued)

*Primary Examiner* — Bruce E Snow
(74) *Attorney, Agent, or Firm* — Sheridan Ross P.C.

(57) ABSTRACT

A voluntary opening prosthetic split hook terminal device is provided with an adjustable pinch force, functional grasping contours and illumination capabilities. Embodiments of the present invention include a tensioning mechanism that permits adjustment of the tension of a spring member to increase or decrease the pinching force of the device. The tensioning mechanism may be repositioned among multiple positions to vary the tension in a spring member. Movement of the tensioning mechanism utilizes principles of mechanical leverage in a way such that the force applied by the spring member does not need to be directly opposed in order to reposition the tensioning mechanism and the tensioning device will automatically lock into a selected position. Additional embodiments include digits with dual internal edges and logarithmic spiral contours for enhanced grasping of objects. Still further embodiments include illumination for functional and aesthetic purposes.

20 Claims, 9 Drawing Sheets

U.S. PATENT DOCUMENTS

| | | | |
|---|---|---|---|
| 2,561,383 | A | 7/1951 | Larkins et al. |
| 2,573,351 | A | 10/1951 | Motis |
| 2,582,234 | A | 1/1952 | Conzelman, Jr. et al. |
| 2,638,604 | A | 5/1953 | Motis |
| 2,641,769 | A | 6/1953 | Robinson |
| 2,692,390 | A | 10/1954 | Motis |
| 2,710,974 | A | 6/1955 | Motis |
| 3,258,784 | A | 7/1966 | Brown |
| 3,604,017 | A | 9/1971 | Brown et al. |
| 3,888,362 | A | 6/1975 | Fletcher et al. |
| 3,932,045 | A | 1/1976 | Hillberry et al. |
| 3,945,053 | A | 3/1976 | Hillberry et al. |
| 4,225,983 | A | 10/1980 | Radocy et al. |
| 4,258,441 | A | 3/1981 | Bell |
| 4,332,038 | A | 6/1982 | Freeland |
| 4,373,517 | A | 2/1983 | Criscuolo |
| 4,377,305 | A | 3/1983 | Horvath |
| 4,503,590 | A | 3/1985 | Girard |
| 4,792,338 | A | 12/1988 | Rennerfelt |
| 4,834,760 | A * | 5/1989 | Richter, Jr. .................. 623/65 |
| 4,865,613 | A | 9/1989 | Rizzo |
| 4,923,477 | A | 5/1990 | Horvath |
| 4,990,162 | A | 2/1991 | LeBlanc et al. |
| 5,116,386 | A | 5/1992 | Scribner |
| 5,219,366 | A | 6/1993 | Scribner |
| 5,549,636 | A * | 8/1996 | Li .................................. 606/206 |
| 5,597,189 | A | 1/1997 | Barbee, Sr. |
| 5,784,979 | A | 7/1998 | Nelson |
| 5,888,235 | A | 3/1999 | Jacobsen et al. |
| 6,010,536 | A | 1/2000 | Veatch |
| D460,858 | S | 7/2002 | Zebe, Jr. |
| 6,443,032 | B1 | 9/2002 | Fujii et al. |
| 6,447,532 | B1 | 9/2002 | Herder et al. |
| 6,605,118 | B2 | 8/2003 | Capper et al. |
| 7,083,584 | B2 | 8/2006 | Coligado |
| 7,150,078 | B2 | 12/2006 | Gijsel et al. |
| 7,341,295 | B1 | 3/2008 | Veatch et al. |
| 7,361,197 | B2 | 4/2008 | Winfrey |
| 2004/0195883 | A1 | 10/2004 | Vrijlandt et al. |
| 2005/0192676 | A1 | 9/2005 | Sears et al. |
| 2005/0216097 | A1 | 9/2005 | Rifkin |
| 2005/0234564 | A1 | 10/2005 | Fink et al. |
| 2006/0112619 | A1 | 6/2006 | Oderwald et al. |
| 2007/0032884 | A1 | 2/2007 | Veatch |
| 2007/0213842 | A1 | 9/2007 | Simmons |
| 2008/0188952 | A1 | 8/2008 | Veatch |
| 2010/0082116 | A1 | 4/2010 | Johnson et al. |

FOREIGN PATENT DOCUMENTS

| | | |
|---|---|---|
| FR | 488300 | 9/1918 |
| GB | 126457 | 5/1919 |
| NL | 1004056 | 3/1998 |
| NL | 1009886 | 2/2000 |
| NL | 1018178 | 12/2002 |
| NL | 1021463 | 3/2004 |
| WO | WO 98/11833 | 3/1998 |
| WO | WO 03/017880 | 3/2003 |
| WO | WO 2004/023863 | 3/2004 |

OTHER PUBLICATIONS

Abstract for Phase I SBIR Contract, National Institute of Children's Health and Human Development (NICHD) Grant IR43HD39046-01, (publication date unknown), 1 p.

Abstract for Phase II SBIR Contract, National Institute of Children's Health and Human Development (NICHD) Grant IR43HD39046-02, (publication date unknown), 1 p.

Amstead, B.H., et al.; "Manufacturing Processes, 7th Ed."; John Wiley & Sons, New York, 1977, pp. 269-270.

Atkins, Diane J., et al.; "Comprehensive Management of the Upper-Limb Amputee"; Chapters 5, 11 and 18; New York Springer-Verlag New York, Inc.; 1989.

Cook, R.D., "Concepts and Applications of Finite Element Analysis, 2nd Ed."; John Wiley & Sons, New York, 1981, pp. 483.

Cupo et al.; "Clinical Evaluation of a New, Above-Elbow, Body-Powered Prosthetic Arm: A Final Report"; Journal of Rehabilitation Research and Development; vol. 35, No. 4, Oct. 1998; pp. 431-446.

Den Boer et al. (1999) "Sensitivity of laparoscopic dissectors, what can you feel?" Surgical Endoscopy, vol. 13, pp. 869-873.

Frey, DD and Carlson, LE, "A Body-Powered Prehensor with Variable Mechanical Advantage"; Prosthetics and Orthotics International, 1994, 18, 118-123.

Frey, DD, et al., "Voluntary-Opening Prehensors with Adjustable Grip Force"; Journal of Prosthetic and Orthotics; vol. 7, No. 4, Fall 1995, pp. 124-130.

Herder JL (1998) "Design of spring force compensation systems", Mechanism and Machine Theory, 33(1-2)151-161 (Abstract only).

Jaspers et al. (2004) "Camera and Instrument Holders and Their Clinical Value in Minimally Invasive Surgery", Surgical Laparoscopy, Endoscopy & Percutaneous Techniques, 14(3)145-52. (Abstract only).

Jaspers et al., (2004) "Mechanical manipulator for intuitive control of endoscopic instruments with seven degrees of freedom", Minimally Invasive Therapy and Allied Technologies, 13(3)191-8 (Abstract only).

Jobin et al., "An Underactuated Prosthesis Finger Mechanism with Rolling Joints", Proceedings of DETC ASME Design Engineering Technical Conferences and Computers and Information in Engineering Conference, Salt Lake City, Utah, Sep. 28-Oct. 2, 2004, DETC2004-57192, pp. 1-11.

Klopsteg, PE, and Wilson, PD (1968); "Human Limbs and Their Substitutes"; New York: Hafner Publishing Co.; pp. 226-229.

Kruit, J, and Cook, JC, "Body-Powered Hand Prosthesis with Low Operating Power for Children"; Journal of Medical Engineering & Technology; vol. 13, No. 1/2, (Jan./Apr. 1989), pp. 129-133.

Landsberger, S, et al. "Child Prosthetic Hand Design: No Small Challenge"; Proceedings of the 1996 Wescon Conference, Wescon, Los Angeles, CA, 1996:236-240.

LeBlanc, M, et al., "Mechanical Work Efficiencies of Body-Powered Prehensors for Young Children"; Journal of the Association of Children's Prosthetic-Orthotic Clinics, vol. 27, No. 3, Winter 1992:70-75.

Meeks, D., and LeBlanc, M., "Preliminary Assessment of Three New Designs of Prosthetic Prehensors for Upper Limb Amputees"; Prosthetics and Orthotics International, 1988, vol. 12, 41-45.

Melendez, D., and LeBlanc, M., "Survey of Arm Amputees Not Wearing Prostheses: Implications for Research and Service"; Journal of the Association of Children's Prosthetics-Orthotics Clinics; vol. 23, No. 3, Autumn 1988; 8 pp.

Northwestern University REP-PRL/Resource Unit, "What Users Want: 1992 Survey and Results," Capabilities, vol. 2, No. 4, Jan. 1993, 15 pp.

Plettenburg, DH and Herder, JL; "Voluntary Closing: A Promising Opening in Hand Prosthetics"; Technology and Disability; 15, 2003:85-94.

Rosenbaum DA, "Human Motor Control, 1st Ed."; San Diego: Academic Press; 1991:43.

Sears, H., "Evaluation and Development of a New Hook-Type Terminal Device"; PhD Dissertation Dept. Of Bioengineering, University of Utah, Jun. 1983.

Tuijthof et al. (2000) "Design, actuation and control of an anthropomorphic robot arm", Mechanism and Machine Theory 35(7); 945-962 (Abstract only).

Tuijthof et al., "Ergonomic handle for an arthroscopic cutter", Minim Invasive Ther Allied Technol. Mar. 2003;12(1):82-90 (Abstract only).

U.S. Department of Health and Human Services Publication FDA 87-4222; "An Introduction to Medical Device Regulations"; pp. 2-3.

Veatch; "A Combination VO/VC Terminal Device with Variable Mechanical Advantage"; ADA Technologies, Inc.; Littleton, Colorado, Feb. 28, 2004; 5 pp.

Visser et al. (2000) "Force directed design of a voluntary closing hand prosthesis", Journal of Rehabilitation Research and Development 37(3)261-271 (Abstract only).

Cook, Theodore A., The Curves of Life, Dover Publications, Inc., New York, NY, 1979; republish of original issued by Constable & Co., London, 1914; pp. 407-432.

"The Open Prosthetics Project: A Versatile Body-Powered Hand", available at http://openprosthetics.org/body-powered, printed May 7, 2009, pp. 1-5.

International Search Report for International (PCT) Patent Application No. PCT/US09/44221, mailed Jul. 7, 2009.
Written Opinion for International (PCT) Patent Application No. PCT/US09/44221, mailed Jul. 7, 2009.

International Preliminary Report on Patentability for International (PCT) Patent Application No. PCT/US2009/044221, mailed Nov. 25, 2010.

* cited by examiner

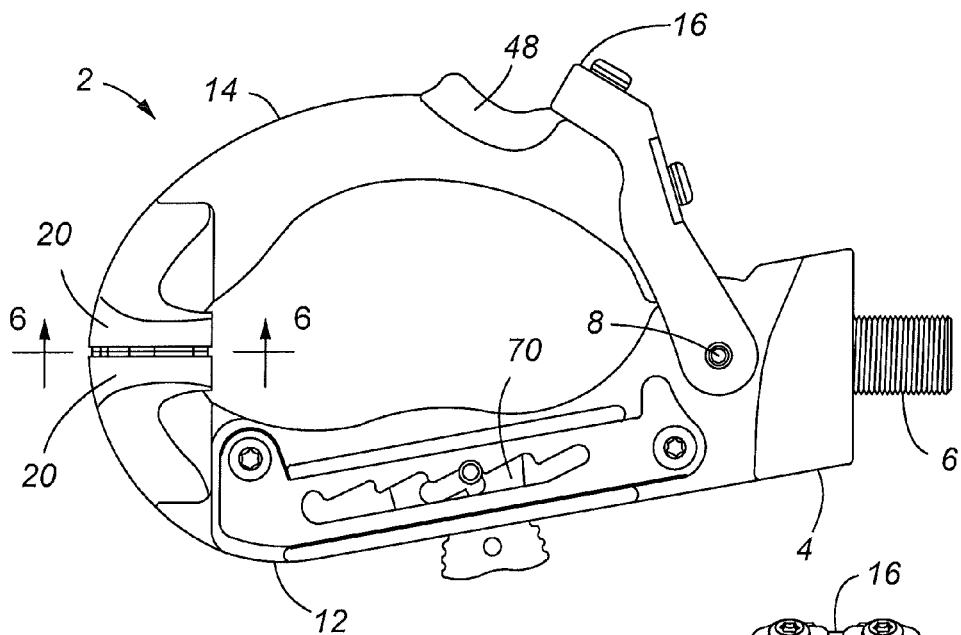
*Fig. 1*
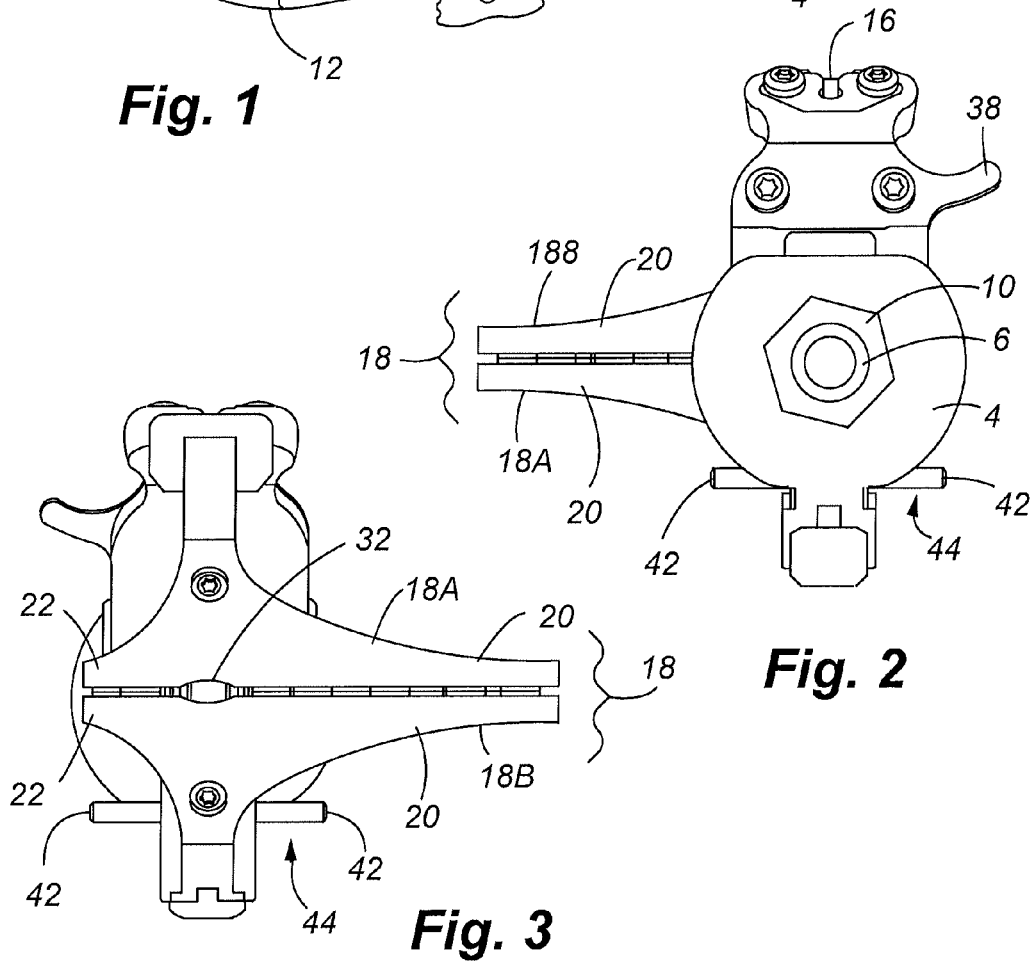
*Fig. 2*
*Fig. 3*

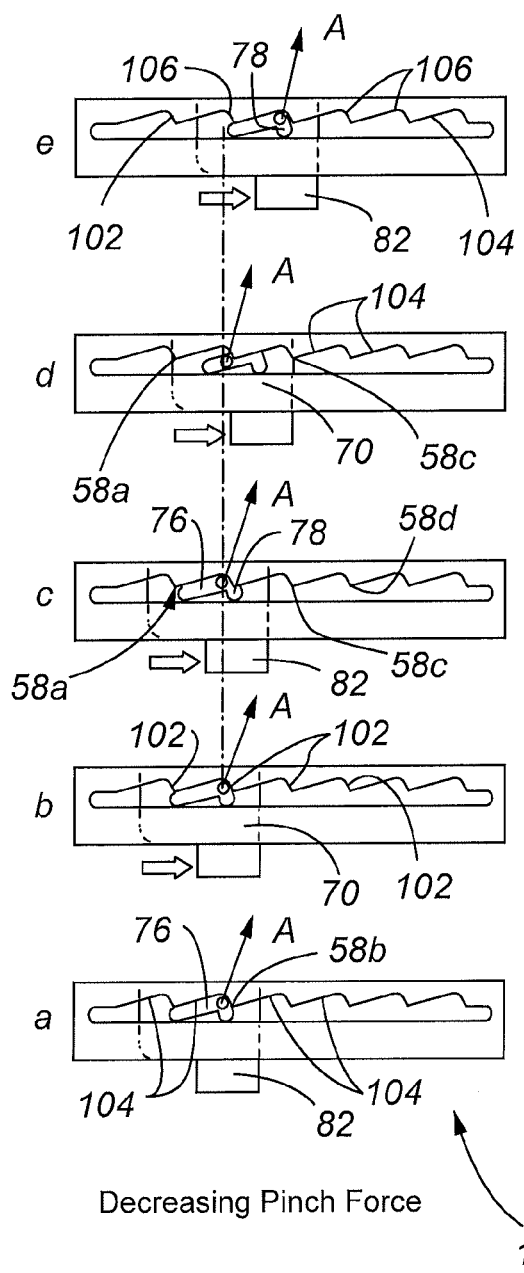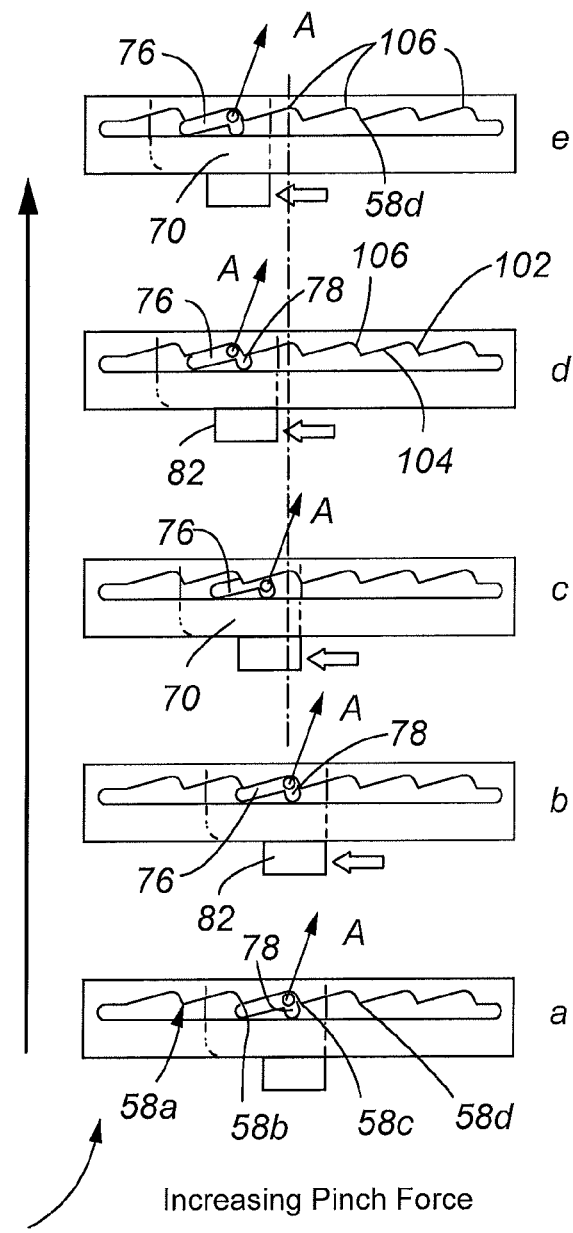
Decreasing Pinch Force    Increasing Pinch Force
Fig. 11    Fig. 12

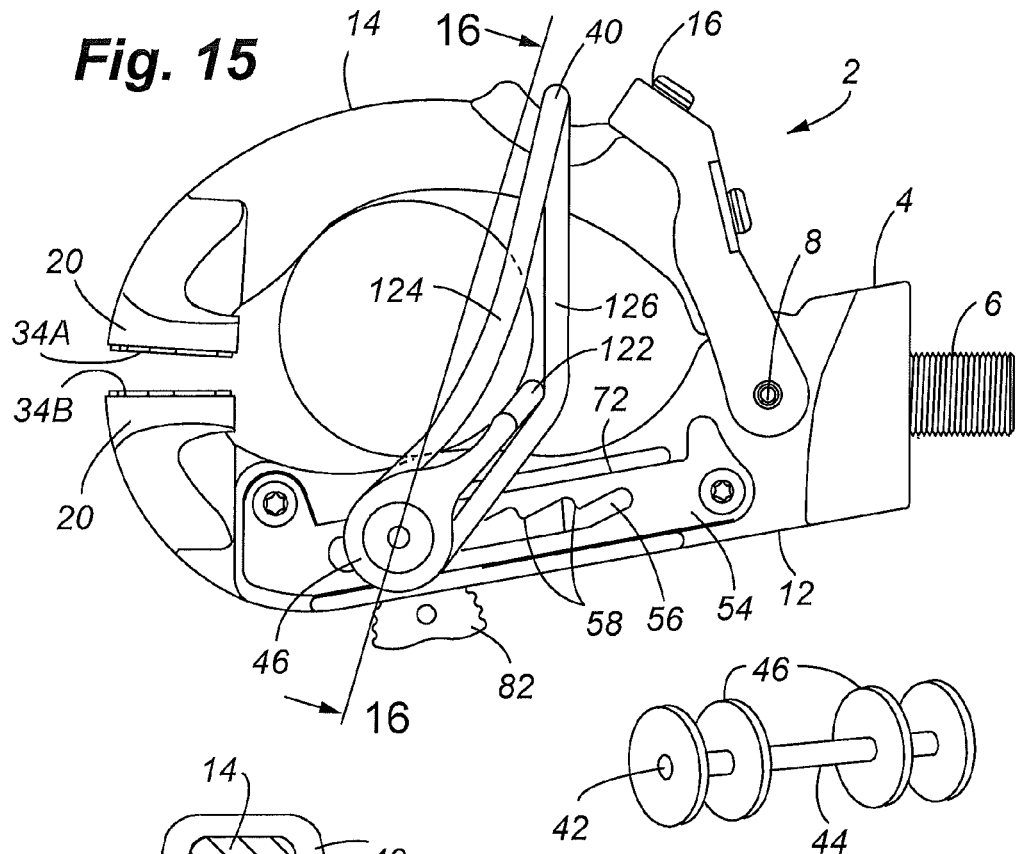
Fig. 15
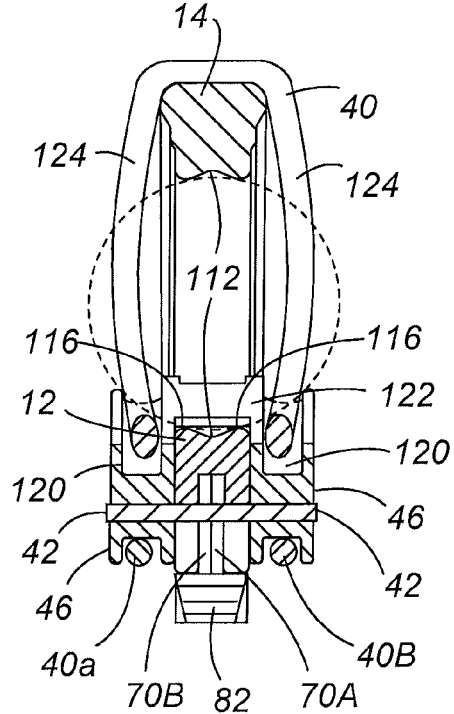
Fig. 16
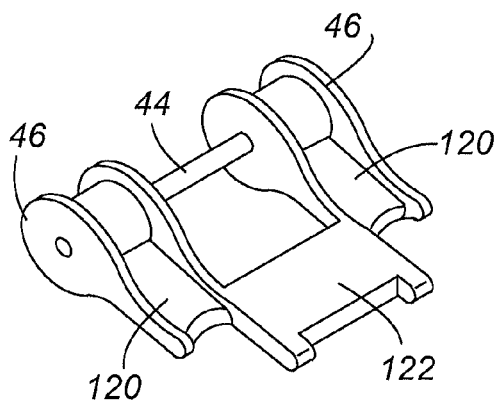
Fig. 14
Fig. 17

PROSTHETIC SPLIT HOOK TERMINAL DEVICE WITH ADJUSTABLE PINCH FORCE, FUNCTIONAL GRASPING CONTOURS AND ILLUMINATION

CROSS REFERENCE TO RELATED APPLICATIONS

The present application claims the benefit of U.S. Provisional Application No. 61/053,537 filed May 15, 2008, the entire disclosure of which is incorporated herein by reference in its entirety.

FIELD

The present application is directed to a voluntary opening prosthesis or terminal device. More specifically, the present application is directed to a split hook type terminal device with a variable or adjustable pinch force, functional grasping contours and/or illumination.

BACKGROUND OF THE INVENTION

A number of prosthetic devices have been developed to assist upper-body amputees, i.e., persons who have lost all or a portion of an upper limb. Although there is a significant need for such devices, many prosthetic devices (artificial arms and/or hands) suffer from poor performance and design.

One type of prosthetic device commonly used is a "body-powered" system. In a body powered system the wearer controls the system using muscles in his or her body, most commonly muscles of the shoulder and neck. Within the realm of body-powered prostheses, there are two primary families of prehensors, differing primarily in their principle of operation. A prehensor, also known as a "gripper" or an "end-effector," is a mechanical prosthetic terminal device used by an upper-body amputee to serve as a replacement for the hand. Voluntary opening (VO) prehensors typically include two or more gripping digits (mechanical fingers) that are held or biased against each other by a spring or one or more custom elastic bands. The user moves the digits apart prior to gripping an object by pulling on a control cable connected to the user's shoulder and neck through a harness. When the user relaxes or eases the tension on the control cable, the digits close on the object to be held and grasp the object. In essence, voluntary opening prehensors are spring loaded clamps that can be opened at will by the user. Therefore, with a voluntary opening prehensor, the wearer's grip on the object is passive and the wearer is not required to expend energy while gripping an object. Unfortunately, since gripping an object with a voluntary opening prehensor is passive, the user has limited, if any, control over the amount of force exerted on the object. Gripping forces needed to lift heavy objects are excessive for small, lightweight or fragile objects. Conversely, the correct gripping force needed to grasp a light object will usually be inadequate for heavier objects. U.S. Pat. No. 3,604,017 issued to Brown et al. and U.S. Pat. No. 5,116,386 issued to Scribner disclose voluntary opening prehensors.

Split hook terminal devices (TDs) are one type of VO prehensor because the grasping digits move apart, or open, as the user increases tension in the control cable. Custom elastic bands or springs affixed to the terminal device cause the device to close and effect grasp as cable tension is reduced, identical in principle to a spring-loaded clamp. Many users who desire increased gripping forces install large numbers of elastic bands to generate high pinch force. While pinch force is increased, substantially larger cable tension is required to cycle or open the terminal device to affect grasp. Repetitive actuation of TDs equipped with excessive bands has been strongly implicated in repetitive stress injuries among upper-extremity amputees in addition to causing excessive equipment wear. Similarly, users may offset a portion of the maximum pinch force by sustaining a counter level of cable tension. While reduced pinch force is achieved, prolonged exposure to the sustained cable tension aggravates repetitive stress injuries. Moreover, the elastic bands typically installed in commercially available TDs are specialized, short, powerful bands that are known in the orthotics and prosthetics industry as being notoriously difficult to install, particularly for amputees. Current commercial VO TDs do not lend themselves to readily changing the number of active bands and, therefore, there is no simple or effective way to easily adjust pinch force as needed or desired.

One example of a VO TD with an adjustable tensioning mechanism is German Patent DE901583. A device is shown in which a metal coil spring extends between two digits. One end of the coil spring is attached to a movable digit and the opposite end of the spring is attached to an adjustment mechanism for altering the location where the spring is attached to the fixed digit. The adjustment mechanism permits the spring to be positioned at a number of different locations on the fixed digit that are all equally spaced from the point at which the spring is connected to the movable digit. The tension in the spring does not change between positions. The adjustment mechanism includes a pin (k) which fits in a pin slot (n) to secure the adjustment mechanism to the fixed digit. Each position provides a different pin slot for locating the pin and securing the position of the adjustment mechanism. The closer the pin location is to the pivot point of the movable digit, the less pinch force is applied by the movable digit. This system has numerous drawbacks including the fact that in order to adjust the position of the coil spring, the pin (k) must be grasped and pulled from the pin hole (n) in a direction directly opposite the force applied by the spring. The adjustment mechanism must then be moved to a new position and the pin inserted into the new pin slot. This requires relatively high strength and dexterity. Further, the coil spring extends across the area in which an object may be grasped, possibly interfering with grasping of an object or damaging the object as a result of the metal spring rubbing against the grasped object.

BRIEF SUMMARY OF THE INVENTION

In accordance with the embodiments of the present invention, a voluntary opening split hook prosthesis or prehensor is provided which allows users a means to easily adjust the pinch force applied by a spring member on one or more digits. Increasing or decreasing the pinch force allows the user to make adjustments as necessary to grasp a variety of objects, taking into account size, weight, fragility and other relevant factors. Embodiments of the present invention allow users to adjust the pinch force to a level appropriate for the task to be accomplished and to do so in a simple and swift manner. This permits the user to achieve the desired level of pinch force sufficiently and reduces the maximum cable tension that must be generated, effectively minimizing wear and tear on the user's own anatomical structures and their equipment while providing a quick and efficient way for the user to vary the pinch force on an as-needed basis.

Embodiments of the present invention utilize an adjustable tensioning mechanism that provides a mechanical advantage to the user. Rather than directly opposing the force applied by the spring member, moving the tensioning mechanism to increase or decrease the tension in the spring member, thereby varying the pinch force, is accomplished by applying a smaller force along an inclined plane. In other words, the tensioning mechanism acts as a simple machine of the wedge class variety. The spring member should be understood to include any suitable closed loop, ring, band, bungee cord, or strap formed of elastomeric materials such that it can generate a pulling force.

In at least one embodiment of the present invention at least one elongated saw-toothed slot and a channel are formed in a fixed digit of the device. A slidable carriage member is positioned in the channel. The carriage member includes an L-shaped slot oriented to parallel the orientation and profile of the saw teeth. A crossbar extends through both the elongated saw-toothed slot and the L-shaped slot of the carriage member. A spring member interconnects at least one end of the crossbar and a movable digit. Each tooth of the saw-toothed slot has a short surface and a long surface and the intersection of the short surface of one tooth with the long surface of an adjacent tooth forms a notch for locating and securing the crossbar. Each different location of the crossbar provides a different tension to the spring member.

The long surface of each tooth faces the pivot point of the movable digit. The short surface of each tooth opposes movement of the crossbar which is continually being pulled by the force of the spring member. Interaction of the crossbar with the surfaces of the sawtooth and the L-shaped slot as the carriage is moved along the channel, together with the force applied to the crossbar by the spring member, allows the position of the tension mechanism to be changed and also causes the tension mechanism to automatically lock into a notch regardless of the location of the tension mechanism relative to the channel or elongate slot. By moving the crossbar in one direction, the spring member is stretched, increasing its tension and generating an increased pinch force. Conversely, moving the crossbar in the opposite direction reduces the length of the spring member and the pinching force is similarly reduced.

The crossbar permits use of a variety of spring members including conventional rubber bands available from office supply stores, eliminating the need to use specialized bands available only from medical supply sources. Users may add or remove as many spring members or rubber bands as they wish to change the pinch force of the device. This allows the user to further adjust the pinch force in addition to adjustments that are provided by the tensioning mechanism. In other embodiments, band spools may be added to the ends of the crossbar to further facilitate placement and removal of spring members from the device. An object support member also may be added to the band spools to provide support for objects grasped by the device. Similarly, the spring members may also support and secure objects grasped within the device. Being made from polymeric materials reduces the likelihood that the spring member will damage or harm the grasped objects unlike metal coil springs.

In other embodiments of the invention the carriage member may be provided with a knob or tab extending from the channel to facilitate adjusting the position of the tensioning mechanism. A user may shift the position of the carriage member and thereby adjust the tension of the spring member simply by pushing or pulling the knob against the edge of a stabilized object, such as the edge of a cabinet, or may engage the knob with their other hand. Accordingly, the pinch force of the device may be adjusted without involvement of the user's opposite hand, making operation of the device simpler for bilateral amputees. The user does not need to use complex body movements to accommodate moving the carriage. In addition, reseating or locking of the crossbar is automatic and does not require a separate coordinated action.

A further advantage of embodiments of the present invention is that the tensioning mechanism is built into one of the grasping digits of the device, minimizing the overall length of the device.

Another advantage of embodiments of the present invention is that it may be fabricated from polymer materials and resins, permitting it to be injection molded. The lightweight polymer materials reduce the overall weight of the device, thereby minimizing inertial effects that may adversely impact balance and movement of the user. A related benefit is that pigments may be added to the polymer materials to achieve desirable coloring, including matching skin tones or to achieve other functional or aesthetic purposes.

In accordance with other embodiments of the present invention, illumination may be added to the device for aesthetic and/or functional purposes. Illumination may make the device more visible and/or may be used to illuminate the area around the device to facilitate grasping of objects in dark environments.

Embodiments of the invention may further include axial openings at the distal ends of the digits to provide a grasping feature for long objects such as pencils, rods, sporting equipment, tools and the like. The openings may be of any shape sufficient to grasp long, relatively thin objects, including cylindrical or frusto-conical, or the opening may be flat-sided such as square, diamond, pentagon or any other shape as appropriate to grasp elongate objects. The device may further be provided with one or more stabilizing arms to assist in supporting objects that are longer than the functional area circumscribed by the digits.

Still further embodiments of the present invention may include a hammerhead hook design at the distal end of the digits to provide forehand and backhand hooking and dragging capabilities. One or more embodiments may include a large hook feature on the medial side and a small hook or shelf-like feature on the opposing or lateral side. Embodiments of the present invention are designed to be adjustable relative to the arm of the user such that the orientation of the device may be changed as desired by the user.

Further embodiments of the present invention also utilize a logarithmic spiral or spira mirabilis to define the various curved surfaces of the device. This provides a visually pleasing appearance and the smooth profile, shapes and contours reduce undesired snagging or hooking the device on other objects.

Various embodiments of the present invention are set forth in the attached figures and in the detailed description of the invention as provided herein and as embodied by the claims. It should be understood, however, that this Summary of the Invention may not contain all of the aspects and embodiments of the present invention, is not meant to be limiting or restrictive in any manner, and that the invention as disclosed herein is and will be understood by those of ordinary skill in the art to encompass obvious improvements and modifications thereto.

Additional advantages of the present invention will become readily apparent from the following discussion, particularly when taken together with the accompanying drawings.

BRIEF DESCRIPTION OF DRAWINGS

The accompanying drawings, which are incorporated in and constitute a part of the specification, illustrate embodiments of the invention and together with the general description of the invention given above and the detailed description of the drawings given below, serve to explain the principles of these inventions.

FIG. 1 is a front elevation view of one embodiment of the terminal device of the present invention, with the spring member removed for clarity.

FIG. 2 is a bottom plan view of the embodiment of FIG. 1.

FIG. 3 is a top plan view of the embodiment of FIG. 1.

FIGS. 11a-e comprise multiple schematic views of components of one embodiment of a tensioning mechanism being adjusted to decrease the pinching force of the movable digit.

FIGS. 12a-e comprise multiple schematic views of components of one embodiment of the tensioning mechanism being adjusted to increase the pinching force of the movable digit.

FIG. 14 is a perspective view of the crossbar of one embodiment of the tensioning mechanism with two band spools positioned at opposite ends of the crossbar.

FIG. 15 is a front elevation view of an alternative embodiment of the terminal device of the present invention shown engaging a spherical object.

FIG. 16 is a partial cross-section view taken along line 16 of FIG. 15 and further showing the spherical object in phantom for clarity.

FIG. 17 is an alternative embodiment of the band spool shown in FIG. 14.

Figure 4:
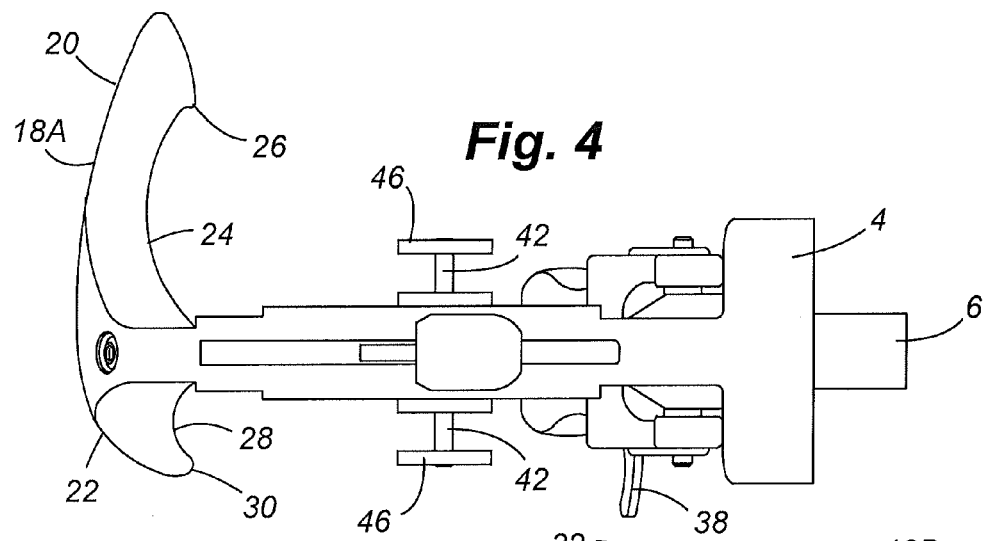
FIG. 4 is a side plan view of the embodiment of FIG. 1, further showing a band spool affixed to each end of a crossbar of the tensioning mechanism, but with the spring member removed for clarity.

It should be understood that the drawings are not necessarily to scale. In certain instances, details that are not necessary for an understanding of the invention or that render other details difficult to perceive may have been omitted. It should be understood, of course, that the invention is not necessarily limited to the particular embodiments illustrated herein.

DETAILED DESCRIPTION OF PREFERRED EMBODIMENT

Turning to FIG. 1, one embodiment of the split hook prehensor or terminal device 2 of the present invention is illustrated. The terminal device (TD) 2 comprises a base portion 4 with a threaded mounting boss 6 extending from the base. The threaded mounting boss extends into the TD and has a transverse hole drilled perpendicular to its axis that engages a pivot pin 8. A lock nut 10 (FIG. 9) applies light tension to the threaded mounting boss 6 and secures the pivot pin 8 from falling out of the assembly. Extending from the base 4 in the opposite direction of the mounting boss 6 is a fixed digit 12 and a movable digit 14. The movable digit 14 pivots about the base 4 at the pivot pin 8, also used to secure the threaded mounting boss 6 into the TD. As shown in FIGS. 1 and 2, the movable digit 14 includes a cable mount 16 for attaching one end of a cable, such as a Bowden cable, the other end of which typically engages a shoulder harness or similar device to permit the wearer or user to utilize shoulder and neck muscle movements to rotate the movable digit 14 in an outward direction about the pivot point 8 to thereby open or separate the two digits. The manner in which the cable is attached to the movable digit is well known to persons of ordinary skill in the art and alternative means of mounting a cable to the movable digit that are known to persons of skill in the art are deemed within the scope of the current invention and may be utilized in place of the illustrated cable mount. Additionally, while two digits are shown in the accompanying drawings, it should be appreciated that the concept of the present invention may be used with three or more digits.

Figure 5:
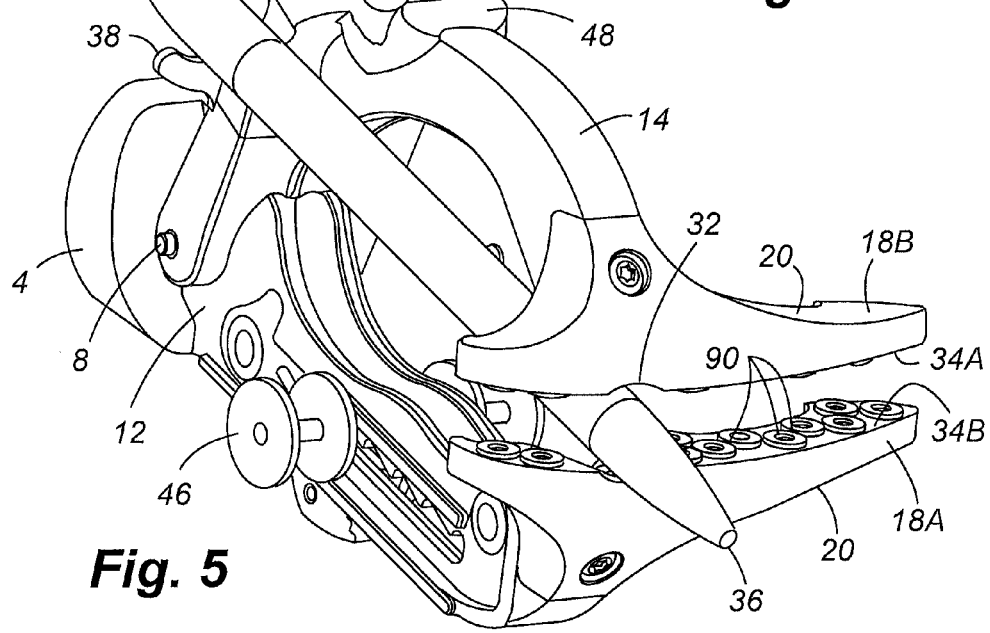
FIG. 5 is a perspective view of the embodiment of FIG. 4 engaging a writing instrument and with the spring member removed.

As shown in FIGS. 3, 4 and 5, a split hook member 18 is positioned at the distal end of the movable and fixed digits. The split hook generally has the shape of a hammerhead and is comprised of two halves 18A and 18B, positioned at the distal end of the fixed digit 12 and movable digit 14, respectively. Each half 18A and 18B comprises a forehand or long hook member 20 and a backhand or short hook member 22. It is intended that the long hook member 20 be medially positioned (facing towards the user) and that the short hook member 22 be laterally positioned (facing away from the user). Of course, the user's preference will determine how the terminal device will be oriented. As best shown in FIG. 4, the lower surface 24 of the long hook member 20 terminates at a barb or tooth 26 to facilitate engaging objects. Similarly, the short hook portion 22 is also curved along the lower surface 28 and also terminates at a tooth or barb 30 to facilitate engaging objects. It should be appreciated that the barbs 26 and 30 may also be eliminated as an alternative embodiment as they may hinder the user's ability to disengage an object once it is engaged. When medially positioned, the long hook portion 20 may be used in a forehand motion to engage an object and when laterally positioned the short hook portion 22 may be used in a backhand motion to engage an object. This design avoids the user having to rotate or adjust the position of the TD for certain grasping tasks, thereby saving time and facilitating use of the TD. Those of skill in the art will also appreciate that the specific configuration of the split hook 18 may be changed to accommodate different or particularized purposes.

Figure 6:
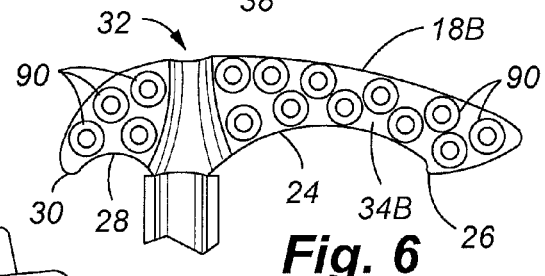
FIG. 6 is a plan view of the inside or abutting surface of the distal end of one digit taken along line 6 of FIG. 1.

With reference to FIGS. 3 and 5, an axial opening 32 may be formed along the mating surfaces 34A and 34B of the two split hook portions 18A and 18B to permit the TD to grasp an elongate object, for example, a writing instrument 36. If the elongate object has a length shorter than the length of the two digits, the object will be held solely by the pinching force applied by the movable digit 14 against the fixed digit 12 at the axial opening 32. If the elongate object has a length greater than the length of the digits, the TD further includes a stabilizing arm 38 which engages and stabilizes the elongate object at a second location spaced from the axial opening. The elongate object will be slightly canted or slanted relative to the two digits. In one embodiment the axial opening 32 may be angled or cone shaped along the inside or abutting surface of each split hook portion, as shown in FIG. 6, to facilitate different orientations of objects grasped at the axial opening 32.

A spring member 40 is employed to maintain a closing tension on the movable digit 14 such that the movable digit 14 is biased to a closed position abutting the fixed digit 12. The spring member 40 may be a coil spring, an elastic strap such as a bungee cord, or a conventional rubber band or any other spring-like device known to those of skill in the art. The spring member 40 may also be a plurality of these type of devices and they also may vary in thickness and size. As should be appreciated, increasing the number of spring members will increase the pinching force generated between the movable digit and the fixed digit. For illustrative purposes only, the spring member shown in FIGS. 7, 8, 15 and 16 is a single closed loop band 40. The opposed ends 40A and 40B of the band engage opposed ends 42 of a crossbar 44 extending through the fixed digit 12. As shown in FIGS. 7, 8, 15 and 16, band spools 46 are positioned on the opposed ends 42 of the crossbar 44 to maintain one or more bands on the crossbar 44. One end of the band engages a first spool 46, wraps around a saddle 48 formed on the movable digit 14, and the opposite end of the band engages a second spool 46 on the opposite end of the crossbar 44. However, it should be appreciated the spools are not required. Alternatively, the ends of the spring members 40 may directly engage the ends of the crossbar 42 as illustrated in FIGS. 1-3.

Figure 9:
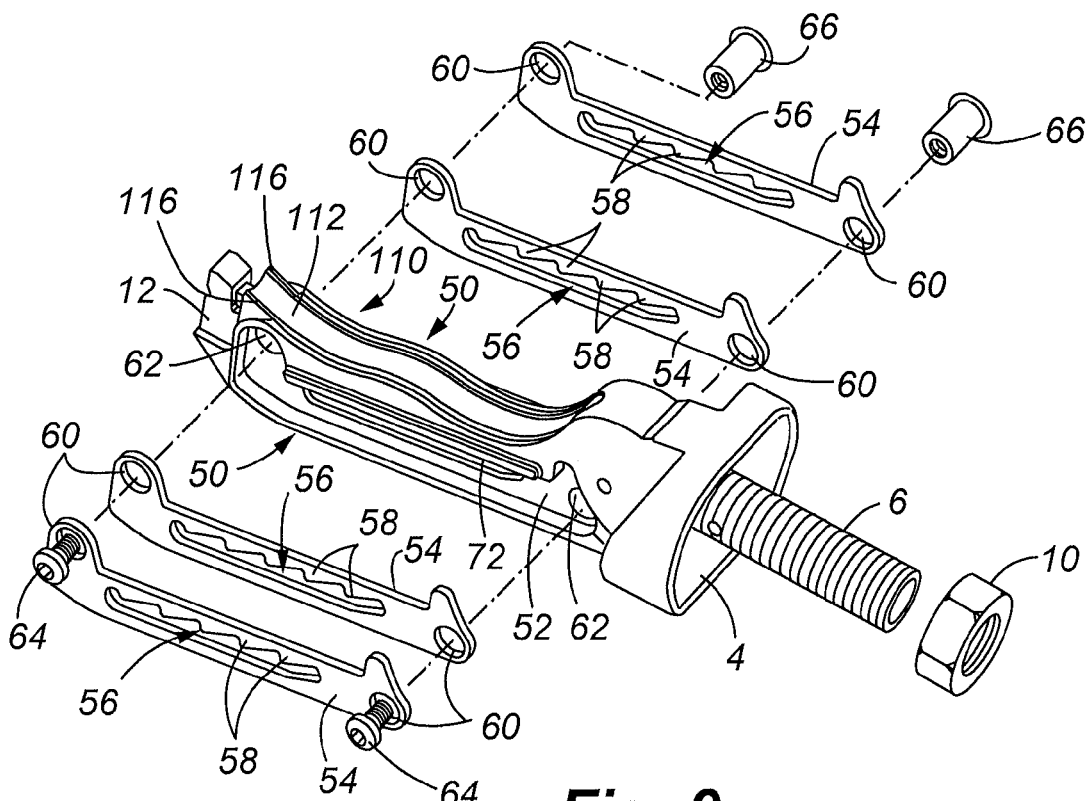
FIG. 9 is an exploded perspective view of the fixed digit of one embodiment of the terminal device of the present invention.
Figure 10:
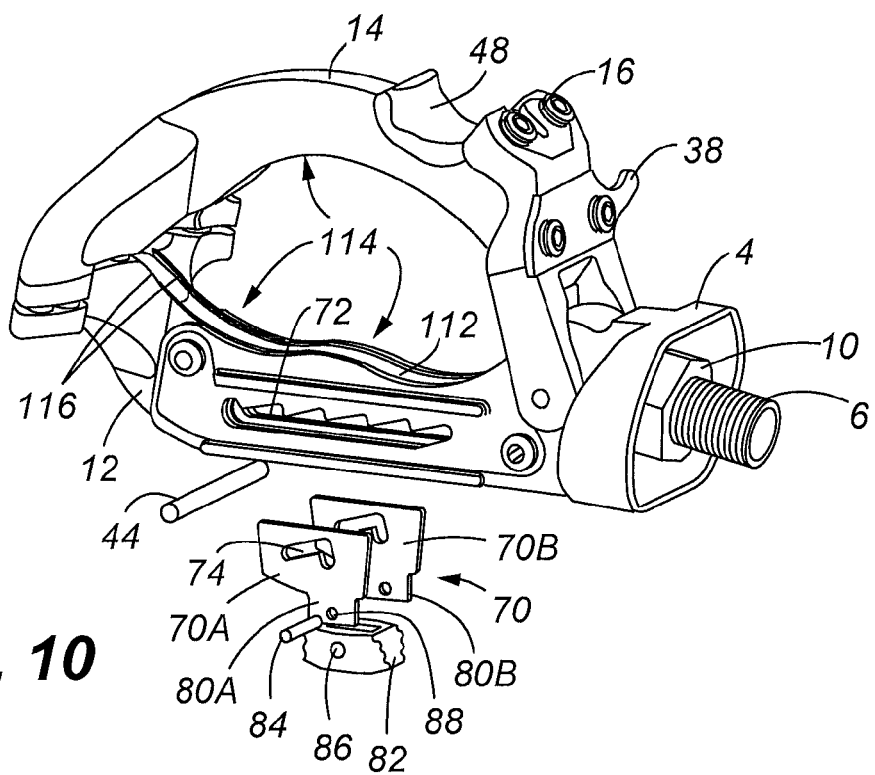
FIG. 10 is a perspective view of the embodiment of FIG. 1 showing components of the tensioning assembly exploded for clarity.

One embodiment of the adjustable tensioning mechanism of the present invention will be described. With reference to FIGS. 9 and 10, the outer side surfaces 50 of the fixed digit 12 include a cut out portion 52. Two metal plates 54 having an elongate slot 56 with a series of angled teeth 58 are positioned in the cut out on both sides of the digit. Those of skill in the art will understand that a single plate may be utilized on each side of the digit to achieve the same result. Openings 60 are formed at each end of each plate 54 and a corresponding bore 62 is formed through the digit such that a mounting screw 64 may extend through each of the plates 54 to engage a complementary internally threaded bushing 66 which extends in the opposite direction through similar openings 60 formed in opposed plates 54 on the opposite side of the digit to thereby secure the plates 54 to the fixed digit 12.

As shown in FIGS. 1 and 10, a carriage member 70 comprising a pair of carriage plates 70A and 70B is positioned in a channel 72 oriented along the longitudinal axis of the fixed digit 12. The carriage plates 70A and 70B include an L-shaped slot 74 with a long leg 76 and a short leg 78. The carriage plates 70A and 70B further include outwardly extending portions 80A and 80B. A knob 82 is positioned over the outwardly extending portions 80A and 80B and a pin 84 is inserted through an opening 86 in the knob 82 and openings 88 in the carriage plates 70A and 70B to secure the knob 82 to the outwardly extending portions 80A and 80B. The knob 82 facilitates movement of the carriage plates 70A and 70B along the channel 72 and presents a larger surface to improve the user's ability to move the carriage plates comfortably. The crossbar 44 extends through the elongated slots 56 in the plates 54 as well as through the L-shaped slots 74 in the carriage plates 70A and 70B to hold the carriage plates in the channel.

Figure 13:
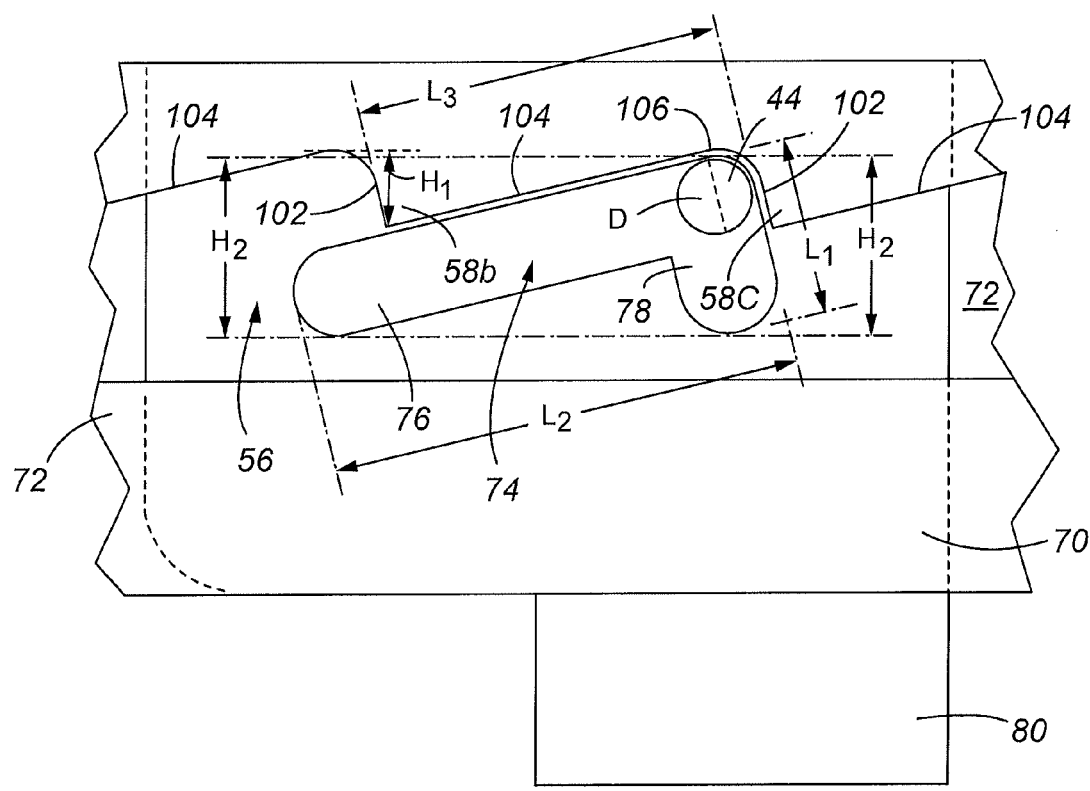
FIG. 13 is an enlarged partial view of the carriage plate, rack plate and crossbar shown in FIGS. 11 and 12.

With reference to FIGS. 11, 12 and 13, adjustment of the tensioning mechanism 100 will be described. The arrowhead A in each figure represents the force or tension being applied to the crossbar 44 by the spring member 40. FIG. 11 represents an action for decreasing the pinching force applied by the movable digit 14, for example moving from the orientation of FIG. 8 to FIG. 7. In comparison, FIG. 12 represents the action of increasing the pinching force applied by the movable digit 14, for example, moving from the orientation of FIG. 7 to FIG. 8. The saw-toothed elongate slot 56 formed in the plates 54 is analogous to a gear rack in a rack and pinion mechanism and the crossbar 44 is analogous to the pinion.

Each elongate slot 56 includes a series or row of spaced-apart teeth 58*a-e*. Each tooth 58 is identically shaped and is formed by a short surface 102 and a long surface 104. With reference to FIG. 13, the crossbar has a diameter D, each tooth has a height $H_1$, the short leg of the L-shaped slot has a length $L_1$ sufficient to give the short leg a height $H_2$, the long leg of the L-shaped slot has a length $L_2$ sufficient to give it a height $H_2$, and long surface of each tooth has a length $L_3$. In this embodiment the following relationship applies: $H_2 \geq H_1 + D$.

With reference to FIGS. 11*a-e*, the crossbar 44 is forced against the short surface 102 of a tooth by the force of the spring member represented by arrow A. As the carriage knob 82 is moved towards the right (moving upwardly in the schematic views FIGS. 11*a→e*), the crossbar 44 is prevented from moving to the right by the force of the spring member pulling the crossbar against the short surface 102 of the tooth 58. As the carriage plate 70 moves to the right, the crossbar 44 engages and rides along the long leg 76 of the L-shaped slot 74 in the carriage plate 70, causing the crossbar 44 to move vertically downward along the short surface 102 of the tooth 58 until such time as the crossbar clears the height $H_1$ of the tooth 58. The long leg 76 must have sufficient length ($L_2$) such that the crossbar 44 can vertically travel the distance $H_2$. At this point, the crossbar 44, acting under the force of the spring member 40, is pulled past the point of the tooth 58 and, provided the distance $L_3$ is sufficiently long, will settle against the short surface 102 of the next adjacent tooth 58 to the right. If the distance $L_3$ is too short, the crossbar 44 may skip past the next adjacent tooth 58*b* and settle against the next further tooth 58*a*. Conversely, FIGS. 12*a-e* illustrate how the pinch force of the movable digit 14 is increased. As shown in FIGS. 12*a-e*, this involves moving the carriage plate 70 to the left. Again, as with FIG. 11, the crossbar 44 is being forced against the short surface 102 of a tooth 58 by the force applied by the spring member 40. As the carriage plate 70 moves to the left, the crossbar 44 is engaged by the lower leg 78 of the L-shaped slot 74 in the carriage plate 70, forcing the crossbar 44 to move to the left in FIG. 12. This causes the crossbar 44 to move along the long surface 104 of the adjacent tooth 58*b* and simultaneously travel vertically downward along the short leg 78 of the L-shaped slot 74 until such time as the crossbar 44 clears the height $H_1$ of the adjacent tooth 58*b*. Given the continual force exerted on the crossbar 44 by the spring member 40, once the crossbar 44 passes over the top of the adjacent tooth 58*b*, it is pulled into the notch 106 formed between the short surface 102 of the adjacent tooth 58*b* and the long surface of the next adjacent tooth 58*a*. Accordingly, the tensioning mechanism 100 permits adjustment of tension in the spring member 40 by laterally moving the carriage plate 70 in one direction or the opposite direction along the elongate slot 56 and without having to directly oppose the force applied by the spring member 40. Using vector force analysis, the force required to move the carriage plate 70 laterally in the elongate slot 56 and laterally relative to the direction of the force applied to the crossbar 44 by the spring member (the direction of arrow A in FIGS. 11 and 12) is less than applying a force directly opposite arrow A. When a large number of rubber bands are used or bands that have an inherently large tension, the force required to unseat and lift the crossbar to clear the teeth can become appreciable. Thus, embodiments of the present invention simplify tension adjustment in this context as well. Additionally, the tensioning mechanism is configured to automatically lock the crossbar member in a secure position regardless of where the carriage plate is positioned.

Figure 7:
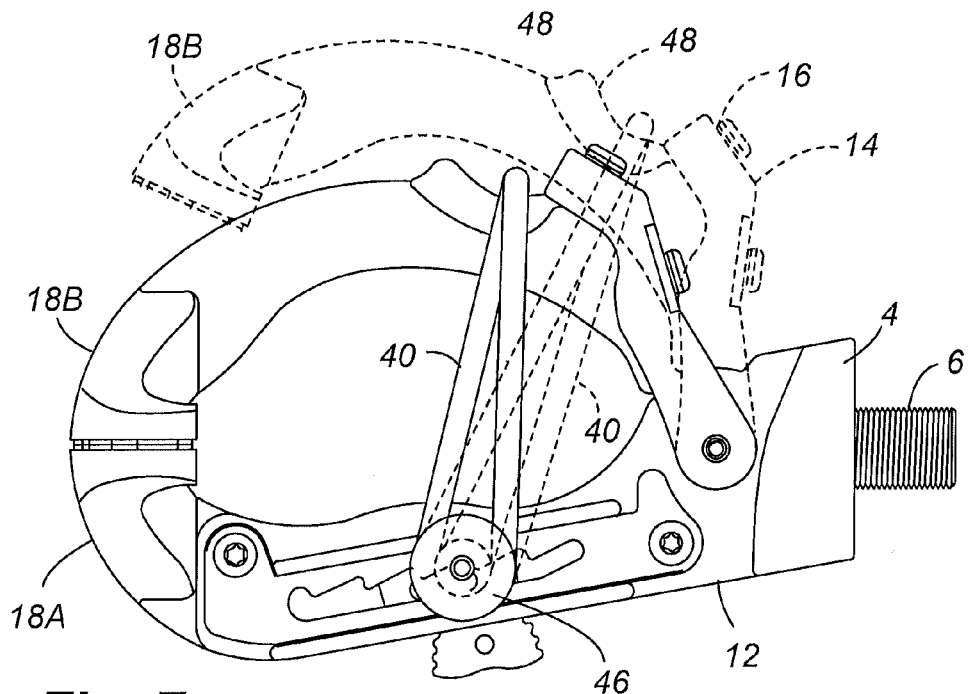
FIG. 7 is a front elevation view of the embodiment of FIG. 4, including a spring member associated with the tensioning mechanism and showing in phantom the movable digit in an open position.
Figure 8:
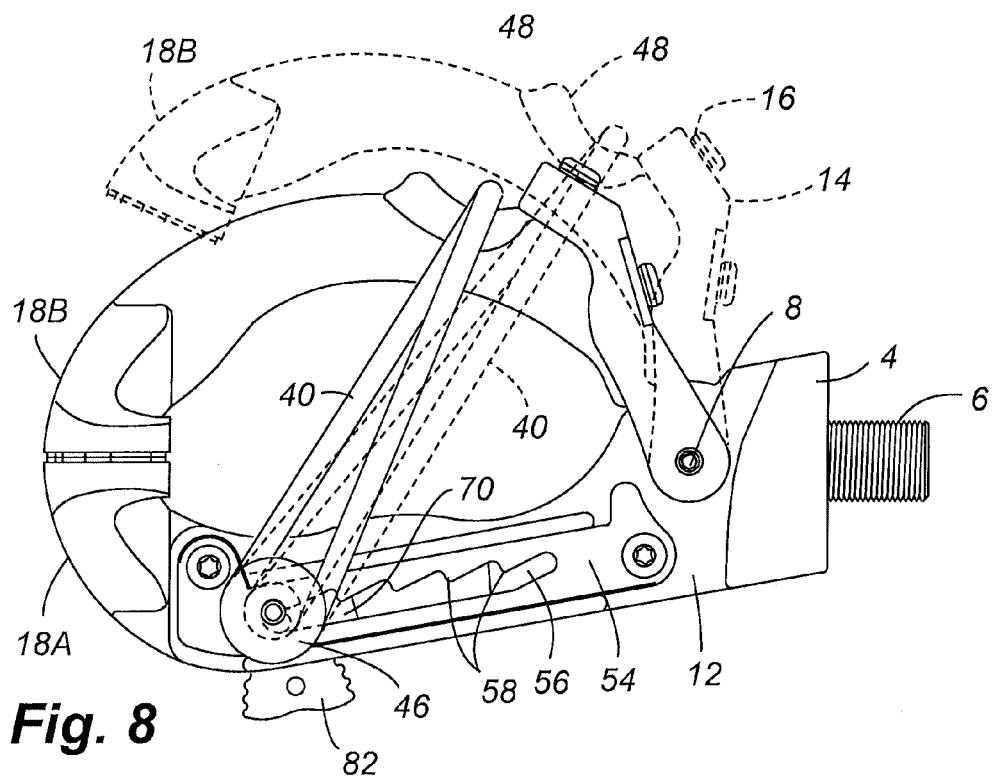
FIG. 8 is a front elevation view of the embodiment shown in FIG. 7 showing the tensioning mechanism at a different setting providing an increased pinching force compared to the embodiment of FIG. 7.

As can be appreciated from FIGS. 7 and 8, as the crossbar 44 moves to the left, the tension on the spring member 40 is increased because its length is increased, thereby increasing pinch force of the movable digit 14. Although the spring constant of the spring member 40 does not change, the energy stored in the spring member increases. Conversely, as the crossbar 44 moves to the right, tension on the spring member 40 is decreased as its overall length of the spring 40 member is decreased, thereby decreasing the pinch force exerted by the movable digit 14. The tensioning mechanism 100 permits the TD's overall pinch force to be adjusted in discrete steps and the mechanism indexes in single increments or multiple increments, as desired, in response to a force applied laterally to the carriage plate. The tensioning mechanism drastically simplifies the ability of the user to increase or decrease the tension on the movable digit solely by moving the carriage laterally, which is particularly helpful to bilateral amputees. For example, the carriage knob 82 may be pressed against any fixed edge such as a door jam, filing cabinet or other secure object, to permit the user to increase or decrease tension without use of the user's opposite hand.

In the embodiments shown, the carriage plate 70 is designed to move in a straight line within channel 72 and along the elongate slot 56 of the plates. In other embodiments, the elongate slot 56 may be curved to follow the contour of the fixed digit. The number of teeth in and/or length of the elongate slot may also be varied to increase or decrease the number of discrete positions of the tensioning mechanism. Alternatively, the tensioning mechanism 100 may be associated with the movable digit 14 rather than the fixed digit 12. As shown in FIGS. 5 and 6, the inside or abutting surfaces 34A and 34B of the split lock 18 may also be provided with pads 90. Depending upon the material used, the pads 90 may cushion a grasped object or have a tackiness that facilitates gripping, or both.

Another advantage of embodiments of the present invention is the ability to more effectively grasp and secure objects, including round or spherical objects, between the opposed digits. As illustrated in FIGS. 9 and 10, the internal surfaces 110 of the movable digit 14 and fixed digit 12 include passive contours 112 that expand the ability of the TD's overall grasping ability. In addition, grooves or channels 114 are formed along the inside surface of the movable digit 14 and fixed digit 12 to create two spaced and parallel edges 116 along the inside surface 110 of each of the digits to improve the grasp of spherical or rounded objects. The parallel edges reduce slipping of objects out of the opposed digits. The edges 116 act to center an object within the opposed digits and increase surface contact area for better grasp. This is illustrated in FIGS. 15 and 16, where a spherical object is held between the movable digit and fixed digit. FIG. 16 shows the spaced parallel edges 116 of the interior surfaces 110 of the fixed digit 12 and movable digit 14 engaging the spherical object. It should also be appreciated that TDs incorporating the concepts of the present invention may be made with differently configured grasping surfaces 110. For example, the internal surfaces may have a customized configuration for grasping a specific object. Where repetitive motions are needed, such as at a job site, a specialized TD may replace a universal TD that the user would normally utilize for daily activities. One or more TDs may be interchangeable.

Additionally, as shown in FIG. 15, the spring member wraps around the spherical object to support and maintain the spherical object within the grasp of the TD. The spring member acts like the web of a human hand, between the thumb and index finger. It interfaces with the grasped object and absorbs vibration, cushions the object, stabilizes the object and, due to the coefficient of friction associated with elastic materials comprising the spring member, provides traction between the spring member and the object to reduce slippage of the object relative to the digits. Because elastic and rubber bands may be utilized instead of a metal coil spring, no damage will be imparted to the grasped object.

An alternative embodiment of the band spool 46, shown in FIG. 17, may be employed to provide additional support to the grasped object. As illustrated in FIG. 17, a platform 120 extends from each of the band spools 46 in a direction parallel to the orientation of the spring member 40. A support platform 122 interconnects the two band spool platforms 120. As installed, the platforms 120 are positioned between two segments 124 and 126 of a closed loop band 40 (FIG. 15). As a result, as the band is deflected by the contour of the object being grasped, the band in turn deflects the orientation of the platforms 120 extending from the band spools 46, causing the support platform 122 to be reoriented as well. Alternatively, the shape of the object being grasped may engage and deflect the support platform 122. In either case, the support platform 122 extends underneath or along a surface of the grasped object providing additional stability.

The embodiments of the TD of the present invention may be fabricated from polymer resins. This allows the component pieces to be molded, resulting in cost savings compared to other methods of manufacture. Further, the polymer resins produce a lighter weight end product which minimizes inertial effects that may adversely impact balance and movement of the user wearing a device of this type. A further attendant advantage is that the resins may be colored to provide the user with a selection of aesthetic choices, including skin tones.

Figure 20:
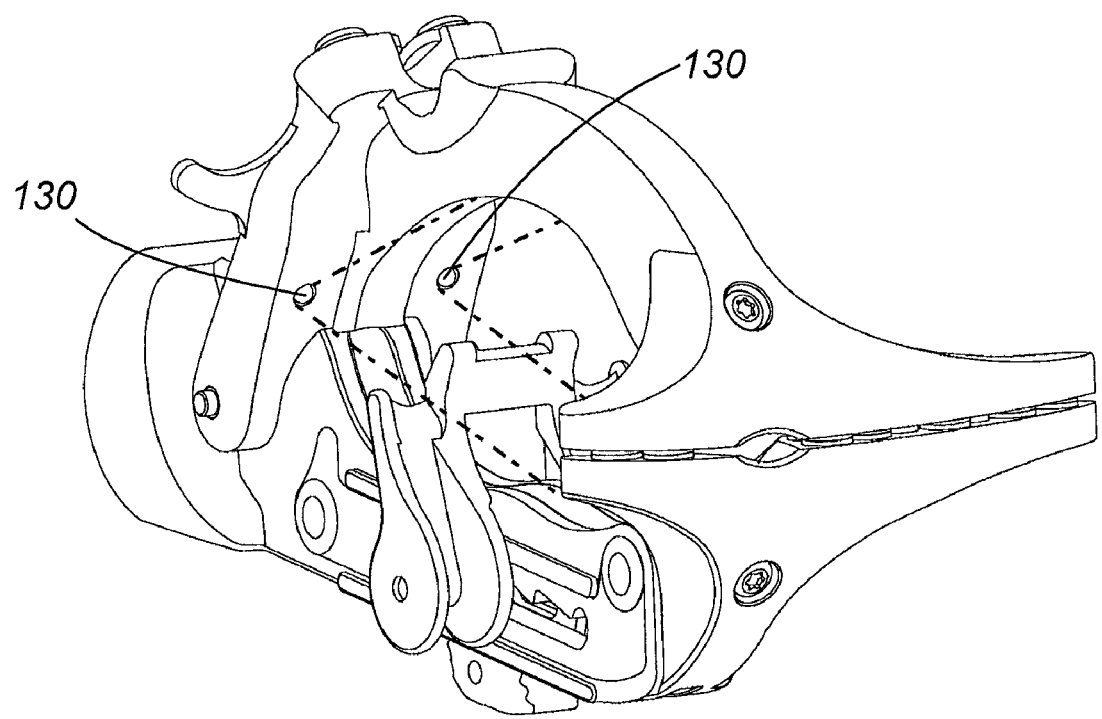
FIG. 20 is a perspective view of an alternative embodiment of the present invention further including an illumination feature.

In addition, the TD may be manufactured from opaque or translucent materials. As illustrated in FIG. 20, embodiments of the present invention may also incorporate a light source 130, as known to those of skill in the art, including light emitting diodes, small incandescent bulbs or other materials, including radioactive forms, that can be charged or stimulated (for example, by exposure to photons or an electrical current), or made to glow or phosphoresce so as to emit light from the surfaces or interior of the components for different purposes. Embodiments may also include small batteries, solar cells, Faraday inductors, shaker magnet electrical energy generators, eccentrically weighted electrical energy generators, or other sources of electrical energy, along with electronic controls to turn light generation on or off, to effect blinking or transitions of color, or to cause flashing or other desired lighting effects. Light may be used for decorative purposes, or to increase or diminish overall visibility of the TD or to direct light to locations in proximity to objects being grasped for increasing visual acuity and/or enhancing utility of the device in unfavourable lighting conditions.

Figure 18:
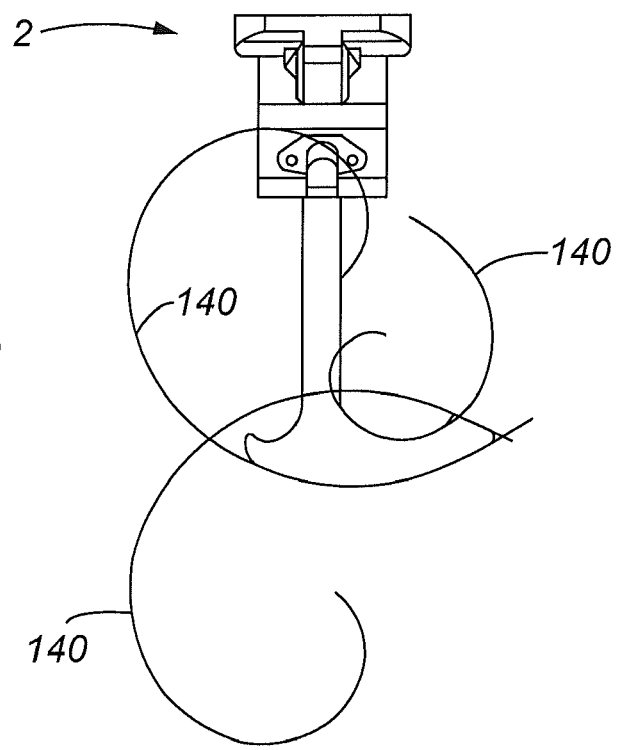
FIG. 18 is a schematic view of one embodiment of the distal end of a split hook digit, with three logarithmic spirals (spira mirabilis) applied to its shape.
Figure 19:
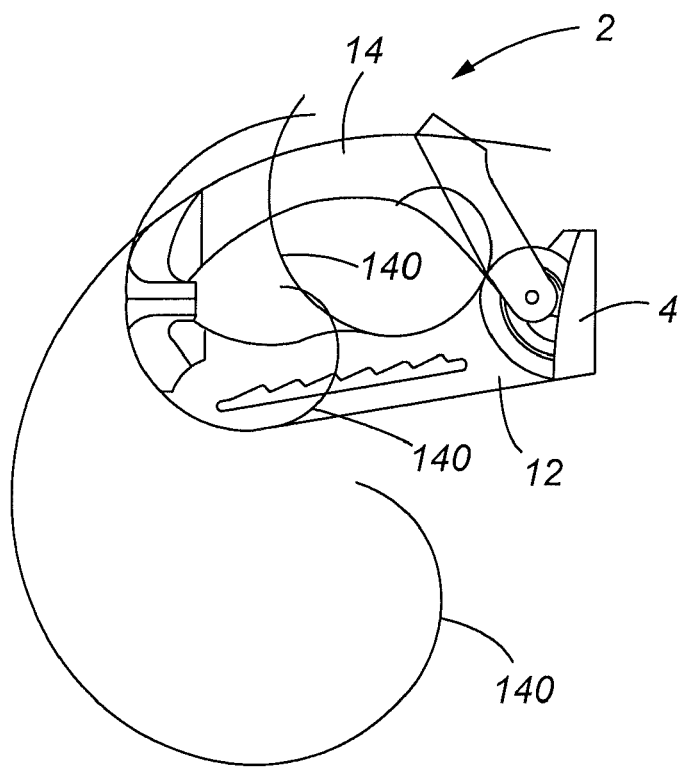
FIG. 19 is a schematic view of one embodiment of the terminal device of the present invention with three logarithmic spirals (spira mirabilis) applied to its shape.

With respect to FIGS. 18 and 19, it can be seen that the design of one embodiment of the present invention uses a logarithmic spiral 140 or spira mirabilis to define various curved surfaces. The use of this spiral and/or portions of it within the design conveys a visually pleasing organic appearance that is consistent with naturally occurring organisms and provides a smooth profile to the shapes and contours of the embodiment. The natural curves provide the functional benefit of eliminating edges that may engage or snag on clothing or other objects.

The present invention, in various embodiments, includes components, methods, processes, systems and/or apparatus substantially as depicted and described herein, including various embodiments, subcombinations, and subsets thereof. Those of skill in the art will understand how to make and use the present invention after understanding the present disclosure. The present invention, in various embodiments, includes providing devices and processes in the absence of items not depicted and/or described herein or in various embodiments hereof, including in the absence of such items as may have been used in previous devices or processes, e.g., for improving performance, achieving ease and\or reducing cost of implementation.

The foregoing discussion of the invention has been presented for purposes of illustration and description. The foregoing is not intended to limit the invention to the form or forms disclosed herein. In the foregoing Detailed Description of the Invention for example, various features of the invention are grouped together in one or more embodiments for the purpose of streamlining the disclosure. This method of disclosure is not to be interpreted as reflecting an intention that the claimed invention requires more features than are expressly recited in each claim. Rather, as the following claims reflect, inventive aspects lie in less than all features of a single foregoing disclosed embodiment. Thus, the following claims are hereby incorporated into this Detailed Description of the Invention, with each claim standing on its own as a separate preferred embodiment of the invention.

Moreover, though the description of the invention has included description of one or more embodiments and certain variations and modifications, other variations and modifications are within the scope of the invention, e.g., as may be within the skill and knowledge of those in the art, after understanding the present disclosure. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A voluntary opening terminal device, comprising:
   a base;
   an elongate movable digit pivotally attached to the base at a proximal end and having a distal end, the movable digit movable between a closed position and an open position;
   an elongate fixed digit attached to the base at a proximal end and having a distal end, the distal end of the fixed digit abutting the distal end of the movable digit when the device is in a closed position;
   at least one spring member interconnecting the two digits, the spring member having a first end and a second end;
   a mechanism associated with one of the two digits and slidable between a plurality of positions spaced along the one digit, and one end of the spring member interconnected to the mechanism such that movement of the mechanism between the plurality of positions changes the force at which the moveable digit closes against the fixed digit, wherein the mechanism automatically locks in a position regardless of where it is positioned, wherein both ends of the spring member are interconnected to the mechanism; and, wherein the mechanism comprises a crossbar that extends through the one digit, the crossbar has a first end and a second end, the first end is interconnected to the first end of the spring member, and the second end is interconnected to the second end of the spring member.

2. The device of claim 1, further comprising an elongate slot positioned on the one digit and having a plurality of teeth extending into the slot wherein each tooth defines a different position of the mechanism.

3. The device of claim 2, wherein each tooth comprises a long surface and a short surface with the short surface defining a different position of the mechanism.

4. The device of claim 1, wherein the spring mechanism is selected from the group comprising a single elastic band, multiple elastic bands and a coiled spring.

5. The device of claim 1, further comprising two hook-shaped members disposed at the distal end of each digit.

6. The device of claim 5, wherein the two hook-shaped members are different in configuration.

7. The device of claim 6, wherein the first hook-shaped member is longer than the second hook.

8. The device of claim 5, wherein the hook-shaped members are disposed substantially perpendicular to the digit.

9. The device of claim 1, wherein each digit comprises an inner side for engaging objects, and wherein the inner side is concave.

10. The device of claim 9, wherein the inner concave side forms a pair of spaced edges for engaging an object.

11. The device of claim 1, further comprising a light source associated with at least one of the movable digit, the fixed digit and the base.

12. The device of claim 11, wherein the light source comprises one selected from the group of light emitting diodes, incandescent bulbs and radioactive forms.

13. The device of claim 1, wherein the spring member forms at least two spaced segments extending between the movable and fixed digits to support a grasped object and reduce slippage of the object relative to the digits.

14. A voluntary opening terminal device, comprising:
   a base;
   an elongate movable digit pivotally attached to the base at a proximal end and having a distal end, the movable digit movable between a closed position and an open position;
   an elongate fixed digit attached to the base at a proximal end and having a distal end, the distal end of the fixed digit abutting the distal end of the movable digit when the device is in a closed position;
   at least one spring member interconnecting the two digits, the spring member having a first end and a second end;
   a mechanism associated with one of the two digits and slidable between a plurality of positions spaced along the one digit, and one end of the spring member interconnected to the mechanism such that movement of the mechanism between the plurality of positions changes the force at which the moveable digit closes against the fixed digit, wherein the mechanism automatically locks in a position regardless of where it is positioned;
   an elongate slot positioned on the one digit and having a plurality of teeth extending into the slot wherein each tooth defines a different position of the mechanism, wherein each tooth comprises a long surface and a short surface with the short surface defining a different position of the mechanism, wherein the mechanism comprises a carriage disposed within a slot formed in the one digit, the carriage having a slot formed herein, and a crossbar having a first end and a second end that extends through the slot in the carriage and through the elongate slot, such that movement of the carriage within the slot formed in the one digit causes the crossbar to engage the elongate slot and the slot formed in the carriage.

15. The device of claim 14, wherein both ends of the spring member are interconnected to the mechanism.

16. The device of claim 14, wherein one of the two digits is the fixed digit.

17. The device of claim 14, wherein the one of the two digits is the movable digit.

18. In a voluntary open terminal device having a fixed digit and a movable digit, the movable digit movable between a first closed position in which the distal ends of the two digits are in contact and a second open position in which the distal ends of the two digits are space apart, a method of adjusting the pressure applied by the movable digit towards the fixed digit comprising:

providing an elongate slot associated with one a digit, the elongate slot having a plurality of spaced apart teeth extending into the slot, each tooth comprising a short surface and a longer ramped surface, the short surface of each tooth interconnecting with the long ramped surface of the next adjacent tooth, wherein a carriage member is positioned adjacent the elongate slot and movable along the path defined by the elongate slot, the carriage member having an angled slot;

providing a crossbar extending through the carriage slot and the angled slot, the crossbar having a first end and a second end;

engaging a first end of a spring member with the first end of the crossbar, such that the spring member is wrapped about the other digit and the second end of the crossbar is engaged with the second end of the spring member; and sliding the carriage along the elongate slot such that the crossbar engages either or both the elongate slot and the angled slot and automatically secures itself against one of the teeth.

19. The method of claim 18, wherein the force applied by the spring member to the crossbar causes the crossbar to automatically engage a tooth as the carriage is moved.

20. The method of claim 18, wherein when the carriage moves in one direction along the elongate slot, the crossbar follows the contour of the elongate slot and when the carriage moves along the elongate slot in the opposite direction the cross bar follows the contour of the angled slot.

* * * * *

UNITED STATES PATENT AND TRADEMARK OFFICE
CERTIFICATE OF CORRECTION

| | | |
|---|---|---|
| PATENT NO. | : 8,052,761 B2 | Page 1 of 1 |
| APPLICATION NO. | : 12/467098 | |
| DATED | : November 8, 2011 | |
| INVENTOR(S) | : Bradley D. Veatch | |

It is certified that error appears in the above-identified patent and that said Letters Patent is hereby corrected as shown below:

In the Specifications:

In column 1, at line 13, please insert the following:

--GOVERNMENT SUPPORT

This invention was made with government support under grant number R44HD058380 awarded by the National Institute of Health (NIH). The government has certain rights in the invention.--

Signed and Sealed this
Twenty-eighth Day of January, 2014

Michelle K. Lee
*Deputy Director of the United States Patent and Trademark Office*